United States Patent
Wei et al.

(10) Patent No.: US 12,400,917 B2
(45) Date of Patent: Aug. 26, 2025

(54) METHOD FOR VERIFICATION OF CONDUCTIVITY TYPE OF SILICON WAFER

(71) Applicants: Zing Semiconductor Corporation, Shanghai (CN); SHANGHAI INSTITUTE OF MICROSYSTEM AND INFORMATION TECHNOLOGY, CHINESE ACADEMY OF SCIENCES, Shanghai (CN)

(72) Inventors: Xing Wei, Shanghai (CN); Minghao Li, Shanghai (CN); Zhongying Xue, Shanghai (CN)

(73) Assignees: Zing Semiconductor Corporation, Shanghai (CN); SHANGHAI INSTITUTE OF MICROSYSTEM AND INFORMATION TECHNOLOGY, CHINESE ACADEMY OF SCIENCES, Shanghai (CN)

( * ) Notice: Subject to any disclaimer, the term of this patent is extended or adjusted under 35 U.S.C. 154(b) by 400 days.

(21) Appl. No.: 17/539,047

(22) Filed: Nov. 30, 2021

(65) Prior Publication Data

US 2023/0037569 A1 Feb. 9, 2023

(30) Foreign Application Priority Data

Aug. 6, 2021 (CN) .......................... 202110902930.6

(51) Int. Cl.
*H01L 21/66* (2006.01)
*G01N 27/12* (2006.01)
(Continued)

(52) U.S. Cl.
CPC ............. *H01L 22/14* (2013.01); *G01N 27/12* (2013.01); *H01L 21/322* (2013.01); *G01N 33/0095* (2024.05)

(58) Field of Classification Search
CPC ... H01L 22/14; H01L 21/3221; H01L 21/324; G01N 27/12; G01N 2033/0095; G01N 27/041; G01R 27/02
See application file for complete search history.

(56) References Cited

U.S. PATENT DOCUMENTS 4,344,815 A * 8/1982 Cazarra ................ G01N 27/041
257/E21.321
5,578,504 A 11/1996 Mitani et al.
(Continued)

FOREIGN PATENT DOCUMENTS

CN 101728262 A 6/2010
CN 113125854 A 7/2021
(Continued)

OTHER PUBLICATIONS

Korean Office Action, dated Oct. 23, 2023 in a counterpart Korean Patent Application No. 10-2021-0171131.
(Continued)

*Primary Examiner* — Eva Y Montalvo
*Assistant Examiner* — Pratiksha Jayant Lohakare
(74) *Attorney, Agent, or Firm* — Chen Yoshimura LLP

(57) ABSTRACT

The present application provides a method for verification of conductivity type of a silicon wafer. The method comprises measuring the resistivity of the silicon wafer to obtain a first resistivity, placing the silicon wafer under atmosphere of air for a predicted time period, measuring the resistivity of the silicon wafer to obtain a second resistivity, and determining conductivity type of the silicon wafer by comparing the first resistivity and the second resistivity. The method can be (Continued)

applied to a silicon wafer having a high resistivity such as higher than 500 ohm$^{-cm}$ to rapidly and accurately determine conductivity type of the silicon wafer. Advantages of the method of the present application include accurate test results, easy operation, simple device requirement, and reduced cost.

6 Claims, 2 Drawing Sheets

(51) Int. Cl.
    *G01N 33/00*     (2006.01)
    *H01L 21/322*     (2006.01)

(56) References Cited

U.S. PATENT DOCUMENTS

| | | | |
|---|---|---|---|
| 6,120,584 A * | 9/2000 | Sakata | B01D 53/0446 96/135 |
| 7,078,919 B2 * | 7/2006 | Prussin | G01R 31/2648 438/18 |
| 11,739,437 B2 * | 8/2023 | Hudson | C30B 15/04 117/13 |
| 2005/0052191 A1 * | 3/2005 | Prussin | G01R 31/2648 324/719 |
| 2005/0158969 A1 * | 7/2005 | Binns | H01L 21/3226 257/E21.32 |
| 2012/0032699 A1 * | 2/2012 | Fukuhara | G01R 31/52 324/762.05 |
| 2014/0379276 A1 * | 12/2014 | Hoshi | H10D 62/834 702/23 |
| 2015/0287630 A1 * | 10/2015 | Qu | H01L 21/02164 438/458 |
| 2018/0114720 A1 * | 4/2018 | Wang | H01L 21/76254 |
| 2020/0002835 A1 * | 1/2020 | Hudson | C30B 29/06 |
| 2021/0050132 A1 * | 2/2021 | Kodama | C22C 33/02 |
| 2022/0146444 A1 * | 5/2022 | Kume | G01N 1/34 |

FOREIGN PATENT DOCUMENTS

| | | | |
|---|---|---|---|
| JP | H07-037953 A | | 2/1995 |
| JP | 2012004439 A | * | 1/2012 |
| JP | 2016-018822 A | | 2/2016 |
| JP | 2020-145306 A | | 9/2020 |
| WO | 2020/139584 A1 | | 7/2020 |

OTHER PUBLICATIONS

Japanese Office Action, dated Mar. 22, 2023 in a counterpart Japanese patent application, No. JP 2021-195892.

Chinese Office Action, dated Jul. 22, 2023, and Search Report dated Jul. 19, 2023, in a counterpart Chinese patent application, No. CN 202110902930.6.

\* cited by examiner

METHOD FOR VERIFICATION OF CONDUCTIVITY TYPE OF SILICON WAFER

BACKGROUND OF THE INVENTION

1. Field of the Invention

The present invention relates to the semiconductor field, and more particularly to a method for verification of conductivity type of silicon wafer.

2. Description of the Related Art

Monocrystalline silicon grown by Czochralski method (CZ method) can be broadly applied to manufacture of semiconductor device. Silicon ingots with various resistivity can be grown by doping. Some device requirements for such as advanced wireless communication applications, insulated gate bipolar transistors (IGBT) and devices with low power and low leakage, request the silicon wafers to have a high resistivity (more than 500 ohm$^{-cm}$). The silicon wafer with high resistance can reduce the influence of parasitic capacitance between devices. The devices can be more densely stacked on the surface of the silicon wafer, and the loss of the signal transmission between devices can be reduced simultaneously.

The silicon wafer with high resistance can obtained by a small amount of doping or non-doping. The carrier concentration is low, e.g. $1\times10^{11}$-$1\times10^{13}$ atom/cm$^3$ while the silicon wafer has a high resistivity, resulting in difficulty on determination of the conductivity type of the carrier. Therefore, the conductivity type has to be verified via measurement. However, the conventional verification methods can be merely applied to silicon wafers with low resistivity, and have disadvantages including inconvenient operation and unreliable test results.

Therefore, there is a need for an improved verification method to solve the above problems.

SUMMARY

To solve the problems in the conventional technologies, the present application provides a method for verification of conductivity type of a silicon wafer comprising: measuring the resistivity of the silicon wafer to obtain a first resistivity, placing the silicon wafer under atmosphere of air for a predicted time period, measuring the resistivity of the silicon wafer to obtain a second resistivity, and determining conductivity type of the silicon wafer by comparing the first resistivity and the second resistivity.

In one embodiment, in the step of determining conductivity type of the silicon wafer by comparing the first resistivity and the second resistivity, the silicon wafer is determined as N-type while the first resistivity is smaller than the second resistivity; and, the silicon wafer is determined as P-type while the first resistivity is larger than the second resistivity.

In one embodiment, before obtaining the first resistivity, the method further comprises conducting a rapid thermal treatment to the silicon wafer to remove thermal donors from the silicon wafer.

In one embodiment, the rapid thermal treatment is conducted at 750° C.-1250° C. for 30 seconds (s)-50 s.

In one embodiment, the first resistivity and the second resistivity of the silicon wafer are measured by using an in-line four-point probe.

In one embodiment, the predicted time period is 1 hour (h)-168 h.

In one embodiment, the silicon wafer has a resistivity of higher than 500 ohm$^{-cm}$.

In one embodiment, the silicon wafer is a monocrystalline silicon wafer.

In one embodiment, the silicon wafer is placed under atmosphere of air for a predicted time period to make natural oxidation and/or chemical adsorption occur on a surface of the silicon wafer.

To solving the problems in the conventional technologies, the present application provides a method for verification of conductivity type of a silicon wafer. In the method, the silicon wafer is placed under atmosphere of air, the first resistivity and the second resistivity of the silicon wafer before and after the placing are measured and then compared to verify the conductivity type. The method can be applied to a silicon wafer having a high resistivity such as higher than 500 ohm$^{-cm}$ to rapidly and accurately determine conductivity type of the silicon wafer. Advantages of the method of the present application include accurate test results, easy operation, simple device requirement, and reduced cost.

DETAILED DESCRIPTION OF THE EMBODIMENTS

Figure 1:
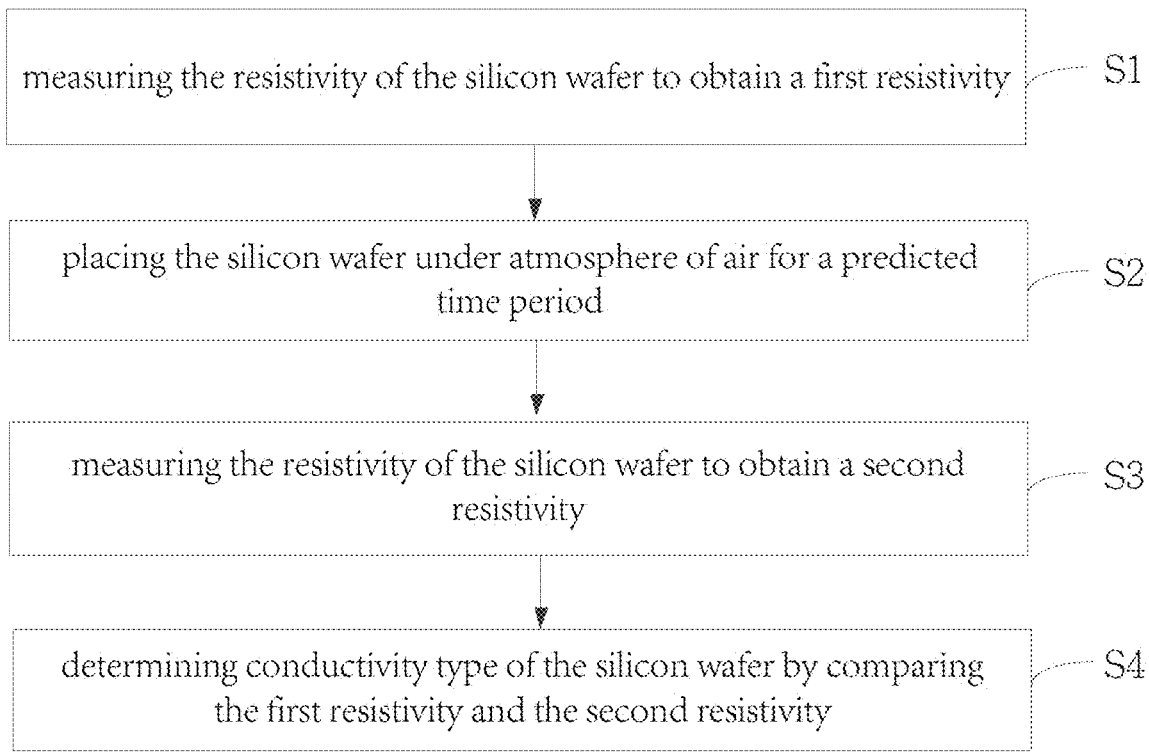
FIG. 1 is a flowchart illustrating method steps for verification of conductivity type of a silicon wafer according to one embodiment of the present application.

To fully understand the present application, detailed structures or steps of the method for verification of conductivity type of a silicon wafer are set forth in the following descriptions to explain the technical solutions of the present application. The implementation of the present application is not limited by the specific detail known by a person having ordinary skills in the art. The preferred embodiments of the present application are described in detail below, but the present application may have other embodiments in addition to the detailed description.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

For easy understanding of the purpose and features of the present invention, the embodiments of the present invention will be further described below with reference to the accompanying drawings. It should be specified that the drawings are provided with very simplified form and imprecise ratios for convenient and clear assistance in explaining the embodiments.

It should be noted that, unless otherwise specified or indicated, the description of the terms "first", "second", and "third" in the specification are only used to distinguish each component, element, step and the like in the specification, but not to indicate the logical relationship or sequence relationship between these components, elements, steps and the like.

Spatially relative terms, such as "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Exemplified embodiments described herein are with reference of the cross-sectional view of the schematic diagram of an idealized embodiment (and intermediate structures) of the present invention. Thus, shape alteration due to, for example, manufacturing techniques and/or tolerances can be expected. Accordingly, embodiments of the present invention should not be limited to the particular shapes of regions illustrated herein but are to include deviations in shapes caused by, for example, manufacturing. Thus, the area shown in figures are substantially schematic and their shapes are not intended to form the actual area of the display device and are not intended to limit the scope of the invention.

The conventional methods for determining conductivity type of a silicon wafer includes the cold-hot probe method and the surface photovoltage method.

The principle for the cold-hot probe method is thermoelectric effect. Two metal probes with different temperature are applied to contact to different parts on the silicon wafer surface, and a galvanometer or a digital voltmeter is applied between the two probes. Based on the direction of the thermoelectric current or the thermoelectric voltage caused by temperature difference between the two contact parts, the conductivity type can be determined. However, this method has better discrimination against thicker samples, needs special equipment, and is more expensive. Further, it is not easy to control the contact between the probes and the silicon wafer, causing inconvenient measurement operation. For silicon wafers with high resistivity, the test results obtained from the cold-hot probe method is unreliable.

In the surface photovoltage method, while light irradiates a silicon sample, non-equilibrium carriers are generated to make a potential change of the surface relative to the inner of the sample. The conductivity type can be determined according to the surface potential difference before and after the light irradiation. However, the presence of static charges or damage layer on the sample surface may affect the test results, and the specific equipment is requested for this method.

There is other methods and equipment for verification of conductivity type of a silicon wafer. For example, a silicon wafer is detected to obtain its actual value of resistance, and the actual value is compared with a setting threshold value of resistance. If the actual value is higher than the threshold value, the silicon wafer is P-type. If the actual value is lower than the threshold value, the silicon wafer is N-type. However, this method is unable to determine a N-type silicon wafer having a resistance of more than $200\Omega$ or a P-type silicon wafer having a resistance of less than $5000\Omega$.

Considering the disadvantages of the conventional measurement methods, the present application provides an improved method for verification of conductivity type of a silicon wafer. In the method of the present application, the silicon wafer is placed under atmosphere of air, the first resistivity and the second resistivity of the silicon wafer before and after the placing are measured and then compared to verify the conductivity type. The method can be applied to a silicon wafer having a high resistivity such as higher than 500 $ohm^{-cm}$ to rapidly and accurately determine conductivity type of the silicon wafer. Advantages of the method of the present application include accurate test results, easy operation, simple device requirement, and reduced cost.

In the present application, the method is applied to monocrystalline silicon wafer. However, the present method can be applied to other types of silicon wafers, which is not limited herein.

In the present application, the method is able to be applied to a silicon wafer having a high resistivity such as higher than 500 $ohm^{-cm}$. The applied scope of the resistivity in the present method is boarder than that in the conventional technologies.

FIG. 1 is a flowchart illustrating method steps for verification of conductivity type of a silicon wafer according to one embodiment of the present application. Referring FIG. 1, the method comprises the following steps.

Step S1: measuring the resistivity of the silicon wafer to obtain a first resistivity, Step S2: placing the silicon wafer under atmosphere of air for a predicted time period, Step S3: measuring the resistivity of the silicon wafer to obtain a second resistivity, and Step S4: determining conductivity type of the silicon wafer by comparing the first resistivity and the second resistivity.

The Step S1 further comprises preparing and selecting a silicon wafer.

In one embodiment, the monocrystalline silicon is grown by Czochralski method (CZ method). A semiconductor crystal growth device comprises a furnace, a crucible located in the furnace, a heater located outside the crucible, silicon melt contained in the crucible. The crucible is consist of a graphite crucible and a quartz crucible sleeved in the graphite crucible. The graphite crucible receives the thermal energy from the heater and melts the polycrystalline silicon materials contained in the quartz crucible to form the silicon melt. By controlling dopants fed into the crucible, a monocrystalline silicon with high resistivity can be grown. In the growing process, the graphite crucible can be used in plural batches of crystal growth but the quartz crucible is replaced by new one for each batch.

A pulling device is set in the top of the furnace. The pulling device drives a seed crystal to pull up the crystal silicon ingot from the melt surface.

The obtained silicon ingot is sliced with a predicted thickness to form silicon wafers.

The Step S1 is conducted by selecting a silicon wafer, and measuring the resistivity of the silicon wafer to obtain a first resistivity.

In one embodiment, in the Step 1, the resistivity of the silicon wafer is measured by using an in-line four-point probe. In one embodiment, the in-line four-point probe is used for measurement of resistivity based on Standard GB/T 1552.

In one embodiment, before obtaining the first resistivity, the method further comprises conducting a rapid thermal treatment to the silicon wafer to remove thermal donors from the silicon wafer.

In the monocrystalline silicon ingot formed by CZ method, a large amount of thermal donors is generated during the following cooling step. It causes increase of the carrier concentration in n-type monocrystalline silicon to reduce its resistivity, and the carrier concentration in n-type monocrystalline silicon is recombined to increase its resistivity and finally converts to n-type silicon. Oxygen source of the silicon wafer is the quartz crucible. Oxygen impurities generate donor effects under the low-temperature thermal treatment. To eliminate the donor effects, the rapid thermal treatment is conducted to the selected silicon wafer to remove the thermal donors.

In one embodiment, the rapid thermal treatment is conducted at 750° C.-1250° C. for 30 seconds (s)-50 s. It should be noted that temperature and time for the rapid thermal treatment are not restricted by the above scope, which can be set depending on situations.

In the Step S2, the silicon wafer is placed under atmosphere of air for a predicted time period.

The predicted time period is not restricted by a specific value or a specific range of values, which can be set depending on situations.

In one embodiment, the silicon wafer is placed under atmosphere of air for 1 hour (h)-168 h (i.e. 1 week). It makes natural oxidation and/or chemical adsorption occur on a surface of the silicon wafer.

Figure 2:
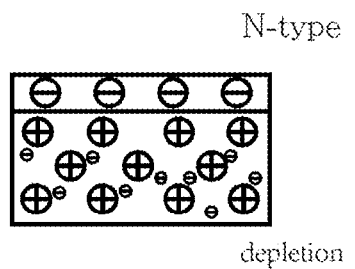
FIG. 2 shows the surface state of the silicon wafer according to one embodiment of the present application.
Figure 2:
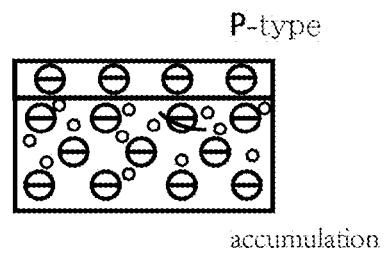

Specifically, as shown in FIG. 2, the silicon wafer shows natural oxidation and/or chemical adsorption to carry negative charges on the wafer surface. Thereby, the surface of the N-type silicon wafer is at depletion status and the resistivity measured by the in-line four-point probe increases. By contrast, the surface of the P-type silicon wafer is at accumulation status and the resistivity measured by the in-line four-point probe decreases. Accordingly, the conductivity type of the silicon wafer can be verified by the change of resistivity before and after the placing, in which the resistivity is measured by in-line four-point probe.

In the Step S3, after the predicted time period of the placing, the resistivity of the silicon wafer is measured to obtain a second resistivity In one embodiment, in the Step 3, the resistivity of the silicon wafer is measured by using an in-line four-point probe. In one embodiment, the in-line four-point probe is used for measurement of resistivity based on Standard GB/T 1552.

In the present application, the conductivity type of the silicon wafer is determined by comparing the first resistivity and the second resistivity.

Figure 3:
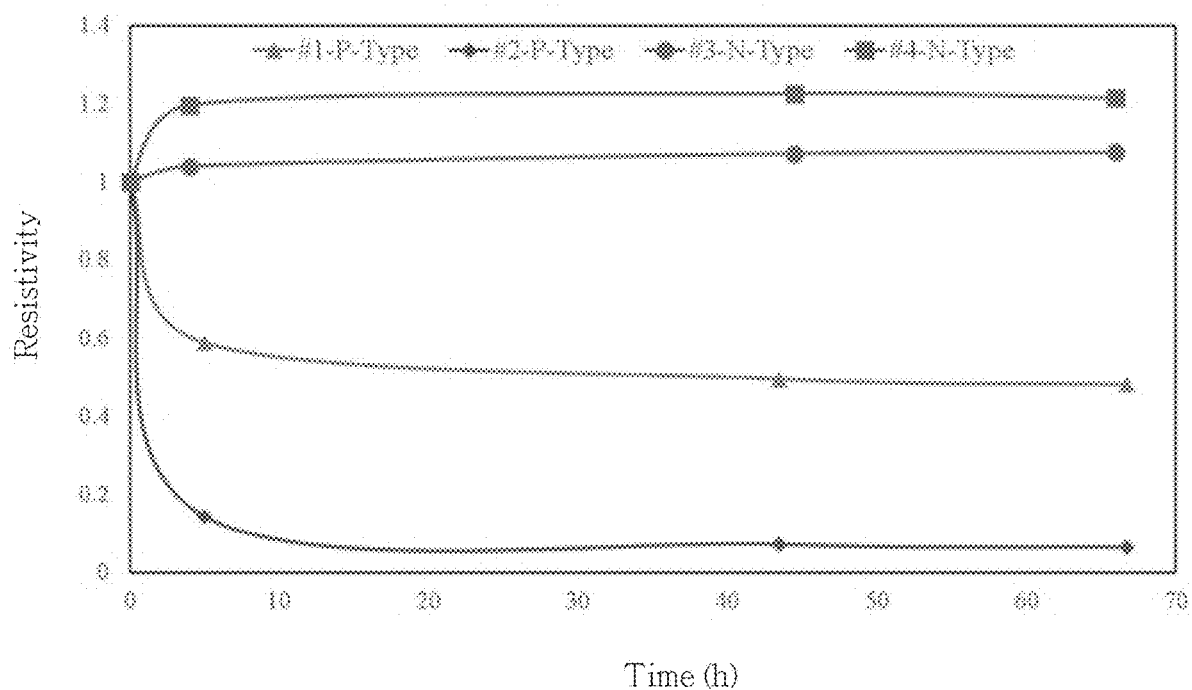
FIG. 3 shows the resistivity changes of the silicon wafers with different conductivity types after being placed for a predicted time period according to one embodiment of the present application.

FIG. 3 shows the tendency of resistivity changes of the N-type and the P-type of the silicon wafers relative to the placing time period. The N-type and the P-type of the silicon wafers have the same initial resistivity. As the time increases, the surface of the N-type silicon wafer is at depletion status, thereby the resistivity gradually increases and tends to be stable. By contrast, as the time increases, the surface of the P-type silicon wafer is at accumulation status, thereby the resistivity gradually decreases and tends to be stable.

For example, after 5 h of storage, the resistivity changes of the N-type and the P-type silicon wafers are shown in the following table.

|  | #1: P-type | #2: P-type | #3: N-type | #4: N-type |
|---|---|---|---|---|
| First resistivity | 5235 | 43175 | 1686 | 1533 |
| Second resistivity | 3079 | 6205 | 1755 | 1834 |

It is known from the above table that the P-type silicon wafer has a decreased resistivity after placing for a period of time, while the N-type silicon wafer has an increased resistivity after placing for a period of time. Accordingly, the type of the silicon wafer can be verified by the resistivity change after the placing for a predicted time period.

In one embodiment, the step S4 of determining conductivity type of the silicon wafer by comparing the first resistivity and the second resistivity comprises:

while the first resistivity is smaller than the second resistivity, the silicon wafer is determined as N-type;

while the first resistivity is larger than the second resistivity, the silicon wafer is determined as P-type.

In the method for verification of conductivity type of a silicon wafer of the present application, the silicon wafer is placed under atmosphere of air, the first resistivity and the second resistivity of the silicon wafer before and after the placing are measured and then compared to verify the conductivity type. The method can be applied to a silicon wafer having a high resistivity such as higher than 500 $ohm^{-cm}$ to rapidly and accurately determine conductivity type of the silicon wafer. Advantages of the method of the present application include accurate test results, easy operation, simple device requirement, and reduced cost.

Those skilled in the art can recognize that the illustrative units or algorithm steps in the above described embodiments can be implemented by hardware, or software, or a combination of hardware and software. The implementation by hardware or software depends on specific application of technical solution and design constraints. Those skilled in the art can implement the described function by applying various means to various specific applications. Such implementation should not be considered to extend beyond the scope of this invention.

Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

It should be appreciated that to simplify the present disclosure and help to understand one or more of the inventive aspects, in the foregoing descriptions of the exemplary embodiments of the present disclosure, features of the present disclosure are sometimes grouped into a single embodiment or figure, or descriptions thereof. However, the methods in the present disclosure should not be construed as reflecting the following intention: that is, the present disclosure claimed to be protected is required to have more features than those clearly set forth in each claim. Or rather, as reflected in the following claims, the inventive aspects aim to be fewer than all features of a single embodiment disclosed above.

Those persons skilled in the art may understand that, unless at least some of such features and/or processes or units are mutually exclusive, all features disclosed in this specification (including the accompanying claims, abstract, and drawings) and all processes or units in any disclosed method or device may be combined by using any combination. Unless otherwise definitely stated, each feature disclosed in this specification (including the accompanying claims, abstract, and drawings) may be replaced with a replacement feature providing a same, an equivalent, or a similar objective.

It should be noted that, unless otherwise specified or indicated, the description of the terms "first", "second", and "third" in the specification are only used to distinguish each component, element, step and the like in the specification, but not to indicate the logical relationship or sequence relationship between these components, elements, steps and the like.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims and its equivalent systems and methods.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims and its equivalent systems and methods.

What is claimed is:

1. A method for verification of conductivity type of a silicon wafer comprising:
   conducting a rapid thermal treatment to the silicon wafer to remove thermal donors before obtaining a first resistivity,
   measuring the resistivity of the silicon wafer to obtain the first resistivity,
   after the measurement of the first resistivity, placing the silicon wafer under atmosphere of air for a predicted time period to make chemical adsorption occur on a surface of the silicon wafer, wherein the predicted time period is 1-168 hours (h),
   after the predicted time period of the placing, measuring the resistivity of the silicon wafer to obtain a second resistivity, and
   determining conductivity type of the silicon wafer by comparing the first resistivity and the second resistivity, wherein the silicon wafer is determined as N-type while the first resistivity is smaller than the second resistivity; and, the silicon wafer is determined as P-type while the first resistivity is larger than the second resistivity,
   wherein the silicon wafer has a resistivity of higher than 500 ohm$^{-cm}$.

2. The method of claim 1, wherein the rapid thermal treatment is conducted at 750° C.-1250° C. for 30-50 seconds(s).

3. The method of claim 1, wherein the first resistivity and the second resistivity of the silicon wafer are measured by in-line four-point probe.

4. The method of claim 1, wherein the silicon wafer has a resistivity of higher than 500 ohm$^{-cm}$.

5. The method of claim 1, wherein the silicon wafer is a monocrystalline silicon wafer.

6. The method of claim 1, wherein the silicon wafer is placed under atmosphere of air for a predicted time period to make natural oxidation on a surface of the silicon wafer.

* * * * *